US011125738B2

(12) United States Patent
Glazier et al.

(10) Patent No.: US 11,125,738 B2
(45) Date of Patent: Sep. 21, 2021

(54) BLOOD SAMPLE ANALYSIS SYSTEMS AND METHODS

(71) Applicant: Thermo Finnigan LLC, San Jose, CA (US)

(72) Inventors: John Glazier, San Jose, CA (US); Jae C. Schwartz, Gilroy, CA (US); Berg A. Tehlirian, Daly City, CA (US)

(73) Assignee: THERMO FINNIGAN LLC, San Jose, CA (US)

( * ) Notice: Subject to any disclaimer, the term of this patent is extended or adjusted under 35 U.S.C. 154(b) by 205 days.

(21) Appl. No.: 16/181,849

(22) Filed: Nov. 6, 2018

(65) Prior Publication Data

US 2020/0141920 A1    May 7, 2020

(51) Int. Cl.
*G01N 33/49* (2006.01)
*G01N 21/47* (2006.01)
(Continued)

(52) U.S. Cl.
CPC ......... *G01N 33/49* (2013.01); *G01N 21/4738* (2013.01); *G01N 33/6848* (2013.01);
(Continued)

(58) Field of Classification Search
CPC .... G01N 33/49; G01N 21/31; G01N 33/6848; G01N 21/4738; H01J 49/0036; H01J 49/0409; H01J 49/0431; H01J 49/26
See application file for complete search history.

(56) References Cited

U.S. PATENT DOCUMENTS 5,633,169 A * 5/1997 Young ................ G01N 33/4925
  436/163
6,887,426 B2   5/2005 Phillips et al.
(Continued)

FOREIGN PATENT DOCUMENTS

EP         2490019 A1    8/2012
WO    WO2010127059 A1   11/2010
(Continued)

OTHER PUBLICATIONS

Carmany et al., "On-substrate Enzymatic Reaction to Determine Acetylcholinesterase Activity in Whole Blood by Paper Spray Mass Spectrometry", Oct. 2018, Journal of The American Society for Mass Spectrometry, vol. 29, pp. 2436-2442. (Year: 2018).*
(Continued)

*Primary Examiner* — Jill A Warden
*Assistant Examiner* — Henry H Nguyen
(74) *Attorney, Agent, or Firm* — Charles B. Katz

(57) ABSTRACT

A system includes an optical measurement unit that measures an optical property of a whole blood sample deposited on a surface of a substrate, an ion source that causes ions derived from the whole blood sample, including ions formed from an analyte of interest present in the whole blood sample, to be emitted from the substrate, a mass analyzer that receives the ions emitted from the substrate and measures an abundance of at least one ion species corresponding to the analyte of interest, and at least one computing device that determines, based on the measured optical property, a hematocrit of the whole blood sample, and determines, based on the determined hematocrit of the whole blood sample and the measured abundance of the at least one ion species, a concentration of the analyte of interest per unit volume of blood plasma.

19 Claims, 10 Drawing Sheets

(51) Int. Cl.
  *H01J 49/00* (2006.01)
  *H01J 49/04* (2006.01)
  *G01N 33/68* (2006.01)
  *H01J 49/26* (2006.01)
  *G01N 21/31* (2006.01)

(52) U.S. Cl.
  CPC ...... *H01J 49/0036* (2013.01); *H01J 49/0409* (2013.01); *H01J 49/0431* (2013.01); *G01N 21/31* (2013.01); *H01J 49/26* (2013.01)

(56) References Cited

U.S. PATENT DOCUMENTS

| | | | |
|---|---|---|---|
| 7,426,407 | B2 | 9/2008 | Higgins |
| 8,759,753 | B1 | 6/2014 | Di Bussolo et al. |
| 9,000,360 | B2 | 4/2015 | DeWitte et al. |
| 9,404,918 | B2 | 8/2016 | D'Aloia et al. |
| 9,911,587 | B1 | 3/2018 | Li et al. |
| 2002/0165439 | A1 | 11/2002 | Schmitt |
| 2013/0171675 | A1 | 7/2013 | Tsukamoto et al. |
| 2015/0118689 | A1* | 4/2015 | Egan .............. A61B 5/14556 435/7.1 |
| 2017/0160273 | A1 | 6/2017 | Nogami et al. |
| 2018/0348194 | A1 | 12/2018 | Boeser et al. |

FOREIGN PATENT DOCUMENTS

| | | |
|---|---|---|
| WO | 2011097343 A1 | 8/2011 |
| WO | 2012170301 A1 | 12/2012 |
| WO | 2017060271 A1 | 4/2017 |
| WO | 2017135952 A1 | 8/2017 |
| WO | 2018217778 A1 | 11/2018 |

OTHER PUBLICATIONS

Capiau et al., "Correction for the Hematocrit Bias in Dried Blood Spot Analysis Using a Nondestructive, Single-Wavelength Reflectance-Based Hematocrit Prediction Method", Analytical Chemistry, vol. 90 (3), 2017, pp. 1795-1804.
Espy et al., "Rapid analysis of whole blood by paper spray mass spectrometry for point-of-care therapeutic drug monitoring," Analyst, 137, 2344-2349, 2012.
Tusa et al., "Critical care analyzer with fluorescent optical chemosensors for blood analytes", J. Mater. Chem., 2005, 15, pp. 2640-2647.
Vogeser et al., "Automated processing of whole blood samples for the determination of immunosuppressants by chromatography liquid tandem-mass spectrometry", Clin Chem Lab Med 2006, vol. 44 (9), pp. 1126-1130.
Wagner et al.: "The use of mass spectrometry to analyze dried blood spots", Mass Spectrometry Reviews, vol. 35 (3), 2016, pp. 361-438.
Wiseman et al., "Direct analysis of dried blood spots utilizing desorption electrospray ionization (DESI) mass spectrometry", Analyst, 2010, 135, pp. 720-725.
Zakaria et al., "Advantages and challenges of dried blood spot analysis by mass spectrometry across the total testing process", The electronic Journal of the International Federation of Clinical Chemistry and Laboratory Medicine, vol. 27 (4), 2016, pp. 288-317.
Capiau et al., "A Novel, Nondestructive, Dried Blood Spot-Based Hematocrit Prediction Method Using Noncontact Diffuse ReflectanceSpectroscopy," Anal. Chem., 2016, 88, pp. 6538-6546.
Miller IV et al,, "An On-card Approach for Assessment of Hematocrit on Dried Blood Spots which Allows for Correction of Sample Volume," J. Anal. Bioanal. Techniques, 8 pgs, 2013.

* cited by examiner

BLOOD SAMPLE ANALYSIS SYSTEMS AND METHODS

BACKGROUND INFORMATION

Blood tests are routinely performed on individuals to monitor physical health, diagnose and monitor illnesses, monitor and manage therapeutic drug treatments, and monitor for illicit use of drugs of abuse, prescription drugs, or performance enhancing drugs. The turnaround time required by clinicians for obtaining and reporting blood test results is generally one hour or less for common blood tests, and can be thirty minutes or less for stat tests. However, laboratories are often unable to provide blood test results within the clinicians' required turnaround times, especially during peak workloads.

Additionally, quality assurance failures have made some blood tests insufficiently reliable for clinical use. For example, assays for hemoglobin A1c, which at high levels can indicate diabetes, are prone to interference from other hemoglobin variants (e.g., hemoglobin S), thus leading to false diagnoses of diabetes or missed cases of diabetes. Similarly, assays for creatinine, which can also signal diabetes as well as renal failure and acute kidney injury, are subject to chemical interference from other substances such as ascorbate, bilirubin, cephalosporins, and dopamine.

Delays and accuracy problems are exacerbated when multiple different analytes are measured, such as when monitoring or managing diabetes or kidney function, because measuring multiple different analytes often requires processing multiple different blood samples by various different methods, often at different locations.

In view of these problems, there exists a need to improve turnaround time for obtaining and reporting blood test results while improving the accuracy of the blood tests.

SUMMARY

In some exemplary embodiments, a system comprises an optical measurement unit configured to measure an optical property of a whole blood sample deposited on a surface of a substrate; an ion source configured to cause ions derived from the whole blood sample to be emitted from the substrate, wherein the ions emitted from the substrate include ions formed from an analyte of interest present in the whole blood sample; a mass analyzer configured to receive the ions emitted from the substrate and measure an abundance of at least one ion species corresponding to the analyte of interest; and at least one computing device configured to determine, based on the measured optical property, a hematocrit of the whole blood sample, and determine, based on the determined hematocrit of the whole blood sample and the measured abundance of the at least one ion species, a concentration of the analyte of interest per unit volume of blood plasma.

In some exemplary embodiments, the optical measurement unit comprises a light source configured to emit light to the whole blood sample, and a light sensor configured to detect at least one of (i) light reflected by the whole blood sample and (ii) light transmitted through the whole blood sample.

In some exemplary embodiments, the light source comprises a light emitting diode (LED), a laser, an incandescent lamp, a discharge lamp, or a combination thereof.

In some exemplary embodiments, the optical measurement unit comprises an optical spectrometer.

In some exemplary embodiments, the ion source includes a voltage source for applying a potential to the substrate.

In some exemplary embodiments, the system further comprises an automated liquid handler for applying a solvent to the whole blood sample.

In some exemplary embodiments, the substrate comprises a layer of porous material such that components of the whole blood sample are transported along the substrate by capillary action after the solvent is added to the whole blood sample.

In some exemplary embodiments, an automated liquid handler further applies one or more of a reagent and an internal standard to the whole blood sample.

In some exemplary embodiments, the substrate is held by a cartridge, the optical unit is further configured to support, during the measurement of the optical property of the whole blood sample, the cartridge in a first position such that light emitted by the optical unit is incident on the whole blood sample, and the ion source is further configured to support, during the emission of the ions from the substrate, the cartridge in a second position such that the ions are delivered to the mass analyzer.

In some exemplary embodiments, the system further comprises a carriage configured to move the substrate from the first position to the second position.

In some exemplary embodiments, the analyte of interest present in the whole blood sample comprises hemoglobin A1c or creatinine.

In some exemplary embodiments, the ions emitted from the substrate further include ions derived from one or more additional analytes of interest present in the whole blood sample, the mass analyzer is further configured to measure an abundance of one or more additional ion species corresponding to the one or more additional analytes of interest, and the at least one computing device is further configured to determine, based on the determined hematocrit of the whole blood sample and the measured abundance of the one or more additional ion species, a concentration of the one or more additional analytes of interest per unit volume of blood plasma.

In some exemplary embodiments, the analyte of interest and the one or more additional analytes of interest comprise components of a renal panel comprising creatinine, total hemoglobin, and an immunosuppressant.

In some exemplary embodiments, the analyte of interest and the one or more additional analytes of interest comprise components of a diabetes panel comprising hemoglobin A1c, creatinine, and total hemoglobin.

In some exemplary embodiments, the analyte of interest and the one or more additional analytes of interest are included in a panel of drugs of abuse.

In some exemplary embodiments, the mass analyzer comprises a quadrupole ion trap mass analyzer, a quadrupole mass filter, a time-of-flight mass analyzer, or an orbital electrostatic trap mass analyzer.

In some exemplary embodiments, the at least one computing device is further configured to provide, for presentation to a user, information indicating the concentration of the analyte of interest per unit volume of blood plasma.

In some exemplary embodiments, the system further comprises an automated liquid handler configured to withdraw the whole blood sample from a volume of whole blood stored in a collection container, and deposit the whole blood sample on the surface of the substrate.

In some exemplary embodiments, a method performed by a blood sample analysis system comprises measuring an optical property of a whole blood sample provided on a surface of a substrate; determining, based on the measured optical property, a hematocrit of the whole blood sample; causing ions derived from the whole blood sample to be emitted from the substrate, the ions emitted from the substrate including ions of an analyte of interest present in the whole blood sample; receiving, at a mass analyzer, the ions emitted from the substrate; measuring, at the mass analyzer, an abundance of at least one ion species corresponding to the analyte of interest; and determining, based on the determined hematocrit of the whole blood sample and the measured abundance of the at least one ion species, a concentration of the analyte of interest per unit volume of blood plasma.

In some exemplary embodiments, an apparatus comprises a light source that causes light to be incident on a whole blood sample deposited on a surface of a substrate; a light sensor that detects, from the whole blood sample, a portion of the light incident on the whole blood sample; an ion source that generates ions from the whole blood sample by directly ionizing the whole blood sample, wherein the ions generated from the whole blood sample include ions formed from an analyte of interest present in the whole blood sample; a mass analyzer that detects, based on a ratio of mass to charge of the ions generated from the whole blood sample, an abundance of at least one ion species corresponding to the analyte of interest; and a physical computing device that determines, based on the detected portion of the light incident on the whole blood sample and the detected abundance of the at least one ion species, a concentration of the analyte of interest per unit volume of blood plasma.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
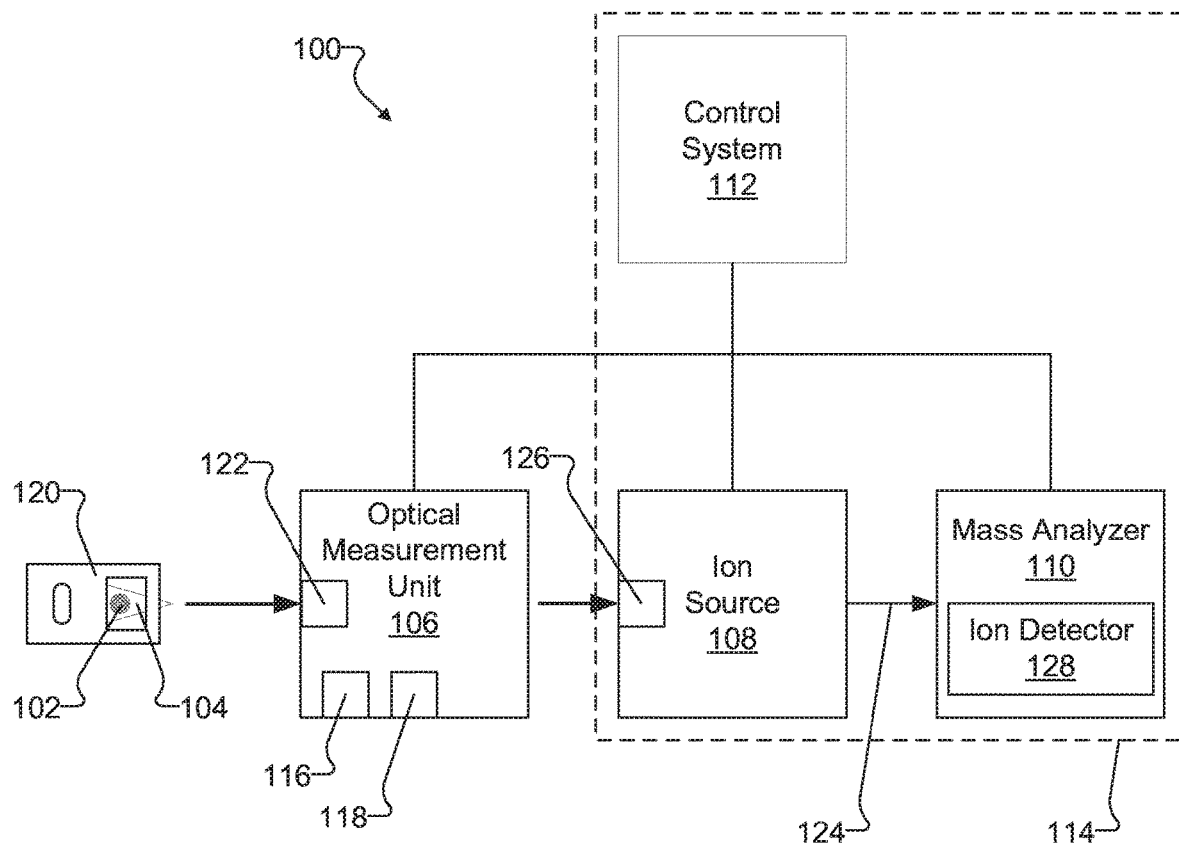
FIG. 1 illustrates an exemplary blood sample analysis system according to principles described herein.

Systems and methods for analyzing a whole blood sample are described herein. In particular, systems and methods for measuring, per unit volume of blood plasma, a concentration of an analyte of interest present in a whole blood sample are described herein. An exemplary system includes an optical measurement unit, an ion source, a mass analyzer, and a control system. The optical measurement unit may be configured to measure an optical property of the whole blood sample deposited on a surface of a substrate. The ion source may be configured to cause ions derived from the whole blood sample to be emitted from the substrate, the ions emitted from the substrate including ions formed from an analyte of interest present in the whole blood sample. The mass analyzer may be configured to receive the ions emitted from the substrate and measure an abundance of at least one ion species corresponding to the analyte of interest. The control system may be configured to determine, based on the measured optical property of the whole blood sample, the hematocrit of the whole blood sample. The control system may also be configured to determine, based on the determined hematocrit of the whole blood sample and the measured abundance of the at least one ion species corresponding to the analyte of interest, a concentration of the analyte of interest per unit volume of blood plasma.

The systems and methods described herein use a mass spectrometer (e.g., an ion source, a mass analyzer, and a control system) to determine an abundance of an analyte of interest present in a whole blood sample per unit volume of whole blood. The mass spectrometer is highly specific and accurate and produces results in short turnaround times. For example, the mass spectrometer can distinguish between different variants of hemoglobin. However, blood test results for most analytes of interest are useful to clinicians only when reported as a concentration per unit volume of blood plasma. Unfortunately, obtaining a concentration of an analyte of interest per unit volume of blood plasma typically requires separating blood plasma from whole blood, such as by centrifugation, a process that significantly prolongs the blood test turnaround time. Moreover, a mass spectrometer used in clinical applications typically requires coupling with a chromatography system to separate the analyte of interest prior to ionization. However, liquid chromatography mass spectrometry systems ("LC-MS") are still unable to meet required turnaround times, and require the use of large amounts of consumables (e.g., columns, packing materials, solvents, calibration kits, etc.).

To eliminate the step of separating blood plasma from the whole blood sample, the systems and methods described herein determine the hematocrit of the whole blood sample and use the determined hematocrit to convert the measurement results of the mass spectrometer (e.g., the abundance of the at least one ion species corresponding to the analyte of interest) into a concentration of the analyte of interest per unit volume of blood plasma. To determine the hematocrit of the whole blood sample, an optical measurement unit measures an optical property (e.g., reflectance and/or transmittance) of the whole blood sample, and the control system determines the hematocrit of the whole blood sample based on the measured optical property. Accordingly, the systems and methods described herein can quickly produce highly accurate blood test results.

Moreover, the systems and methods described herein determine the hematocrit of the whole blood sample based on a measured optical property of the whole blood sample, thereby avoiding contact with the whole blood sample. As a result, ions can be generated directly from the whole blood sample deposited on the surface of the substrate and emitted into the mass spectrometer. Accordingly, the whole blood sample deposited on the surface of the substrate may be used in an integrated process to determine both the hematocrit of the whole blood sample and the abundance of the analyte per unit volume of whole blood, which together may be used to determine the concentration of the analyte of interest per unit volume of blood plasma. With the blood test systems and methods described herein, blood tests that once took hours or days to perform can now be performed in a manner of minutes and can easily meet required turnaround times while producing results with high specificity and accuracy.

The systems and methods described herein may also enable quick and comprehensive monitoring and testing of various illnesses or health conditions with only a single blood sample. As an example, the systems and methods described herein may use a single blood sample to monitor kidney function by multiplexing creatinine measurement with therapeutic drug monitoring. To illustrate, a renal panel may measure a creatinine level to check for renal failure, measure a hematocrit level (or total hemoglobin) to check for renal hemorrhaging, and measure a concentration of one or more therapeutic drugs (e.g., immunosuppressants) to determine the effectiveness of the therapeutic drugs. Such a renal panel can be used, for example, to monitor the efficacy and condition of a kidney transplant in a patient. In this way, the systems and methods described herein can quickly and accurately obtain comprehensive kidney function information from a single blood sample.

As another example, the systems and methods described herein may use a single blood sample to diagnose and/or monitor diabetes. To illustrate, a diabetes panel may measure a level of hemoglobin A1c to detect and/or determine a condition of diabetes, measure a creatinine level to determine if diabetes has progressed to cause renal failure, and measure total hemoglobin to determine if renal failure has progressed to cause anemia. In this way, the systems and methods described herein can quickly and accurately obtain information about a state of diabetes in a patient from a single blood sample.

Other uses and benefits of the systems and methods described herein will be evident from the description that follows.

FIG. 1 illustrates functional components of an exemplary blood sample analysis system 100 ("system 100"). The exemplary system 100 is illustrative and not limiting. System 100 is configured to measure, from a whole blood sample 102 deposited on a surface of a substrate 104, a concentration of an analyte of interest present in whole blood sample 102 per unit volume of blood plasma.

As used herein, an "analyte of interest" refers to any substance present in blood, whether endogenous or exogenous. Examples of analytes of interest may include, without limitation, glucose, hormones (e.g., estrogen, insulin, steroids, testosterone, etc.), lipids (e.g., LDL-cholesterol, HDL-cholesterol, triglycerides, etc.), peptides (e.g., C-peptide), proteins (e.g., albumin, creatinine, hemoglobin, hemoglobin A1c, immunoglobulins, etc.), therapeutic drugs (e.g., antibiotics, analgesics, immunosuppressants, etc.), drugs of abuse (e.g., amphetamines, barbiturates, benzodiazepines, cannabinoids, cocaine, methadone, methaqualone, opiates, phencyclidine, etc.), performance-enhancing drugs (e.g., caffeine, steroids, etc.), drug metabolites, and the like.

As shown in FIG. 1, system 100 includes an optical measurement unit 106, an ion source 108, a mass analyzer 110, and a control system 112. Collectively, ion source 108, mass analyzer 110, and control system 112 may constitute or be implemented by a mass spectrometer 114.

Optical measurement unit 106 includes a light source 116 configured to emit visible and/or non-visible light (e.g., infrared, near-infrared, ultraviolet, and near-ultraviolet light) to whole blood sample 102 and illuminate whole blood sample 102. Light source 116 may be configured to emit a spectrum of light (e.g., white light) and/or light at one or more discrete wavelengths. Light source 116 may be implemented by any suitable light source or light sources, including but not limited to devices that emit polychromatic radiation (e.g., an incandescent lamp or a discharge lamp) and/or devices that emit monochromatic radiation (e.g., a laser or a light emitting diode ("LED")).

Optical measurement unit 106 also includes a light sensor 118 configured to detect, from whole blood sample 102, at least a portion of the light emitted to whole blood sample 102 and measure the intensity of the light detected from whole blood sample 102. For example, light sensor 118 may be configured to detect the portion of the emitted light that is reflected by whole blood sample 102. In some examples, to improve accuracy of the optical measurement, light sensor 118 may be configured to detect only diffusely reflected light from whole blood sample 102 and not specularly reflected light from whole blood sample 102. To this end, light source 116 may be configured such that the emitted light is incident on the surface of whole blood sample 102 at an angle relative to a surface of substrate 104. Light sensor 118 may be positioned outside of the path of specularly reflected light so as to not detect the specularly reflected light from whole blood sample 102.

Additionally or alternatively, light sensor 118 may be configured to detect the portion of emitted light that is transmitted by whole blood sample 102. For example, substrate 104 may be at least partially light-transmissive, such as glass, and light sensor 118 may be positioned on a side of substrate 104 opposite to the surface on which the emitted light is incident to thereby detect the portion of emitted light that is transmitted by whole blood sample 102.

In some examples, light sensor 118 may be configured to detect light at one or more discrete wavelengths. For instance, light sensor 118 may include one or more filters to expose light sensor 118 only to a discrete wavelength or a discrete band of wavelengths, and thereby detect the reflectance and/or transmission of the discrete wavelength(s) from whole blood sample 102.

Light sensor 118 may be implemented by any one or more suitable sensors, including but not limited to a charge-coupled device ("CCD"), a grating spectrometer (e.g., a Czerny-Turner sensor), and the like. In some examples, optical measurement unit 106, including light source 116 and light sensor 118, may be implemented by an optical spectrometer.

In some examples, optical measurement unit 106 may be configured to shield whole blood sample 102 from ambient light (i.e., any light not emitted to whole blood sample 102 by light source 116) that might otherwise interfere with the light detected by light sensor 118. To this end, optical measurement unit 106 may further include, for example, a shield (not shown) configured to block ambient light from illuminating whole blood sample 102. In some examples, the shield may be formed of an opaque material that blocks ambient light. Additionally or alternatively, the shield may include one or more filters configured to block ambient light having the discrete wavelength(s) emitted by light source 116 and/or detected by light sensor 118. Optical measurement unit 106 may further include other optical components as may suit a particular implementation, including but not limited to optical waveguides, fibers, lenses, filters, and the like.

As mentioned above, optical measurement unit 106 is configured to measure an optical property of whole blood sample 102 deposited on the surface of substrate 104. Substrate 104 may be any suitable substrate that is configured to support whole blood sample 102 for measurement of the optical property of whole blood sample 102 and for use by ion source 108 to generate ions from whole blood sample 102 and emit the ions from substrate 104. For example, substrate 104 may be formed of a porous or semi-porous material that absorbs whole blood sample 102 and allows movement of an analyte of interest to a tip end of substrate 104 by capillary action. Exemplary substrates may include, without limitation, paper (e.g., filter paper such as cellulose filter paper, ashless filter paper, nitrocellulose paper, glass microfiber filter paper, and polyethylene paper), fiber, carbon fiber, cloth, a polymer material, and the like. Alternatively, substrate 104 may be formed of a non-porous material such as glass, plastic, metal, or a porous material coated with a hydrophobic film, etc. Substrate 104 may be opaque, transparent, or translucent, as may suit a particular implementation.

In some examples substrate 104 may have a substantially flat, plate-like form, such as a paper substrate used in paper spray ionization or a glass plate. However, substrate 104 is not limited to this form, and may have any other form or shape as may suit a particular implementation, such as but not limited to a cuvette or a swab (e.g., a cotton swab). In some examples, substrate 104 may be held by or within a cartridge 120 configured to support substrate 104 during processing of whole blood sample 102 within system 100. Cartridge 120 helps prevent contamination of whole blood sample 102 by eliminating contact with whole blood sample 102 and substrate 104. Cartridge 120 may have any form or configuration as may suit a particular implementation.

Optical measurement unit 106 may include a cartridge mount 122 configured to hold cartridge 120 in a first position such that light emitted by light source 116 is incident on whole blood sample 102 and reflected or transmitted light from whole blood sample 102 is detected by light sensor 118. Thus, when cartridge 120 is in the first position, optical measurement unit 106 may measure the optical property of whole blood sample 102 deposited on the surface of substrate 104 held by cartridge 120.

Cartridge mount 122 may include any structures (e.g., docks, racks, trays, snaps, locks, etc.) for positioning and supporting the cartridge in the first position. Accordingly, cartridge 120 may have a shape or structure that complements the corresponding cartridge mount 122 included in optical measurement unit 106. Cartridge 120 may be positioned within cartridge mount 122 either manually or automatically, such as by a sample handling mechanism, as will be described below in more detail.

Ion source 108 is configured to generate ions from whole blood sample 102 deposited on the surface of substrate 104 and cause the ions to be emitted from substrate 104 toward mass analyzer 110 as ion beam 124. Ion source 108 may generate the ions from whole blood sample 102 and emit the ions from substrate 104 by any suitable ionization technique. In some examples, ion source 108 may be implemented by a paper spray ion source in which ions derived from an analyte of interest present in whole blood sample 102 are electrosprayed from substrate 104 (see Jiangjiang Liu et al., "Development, Characterization, and Application of Paper Spray Ionization", Analytical Chemistry, Vol. 82, No. 6 (2010), incorporated herein by reference).

Figure 2:
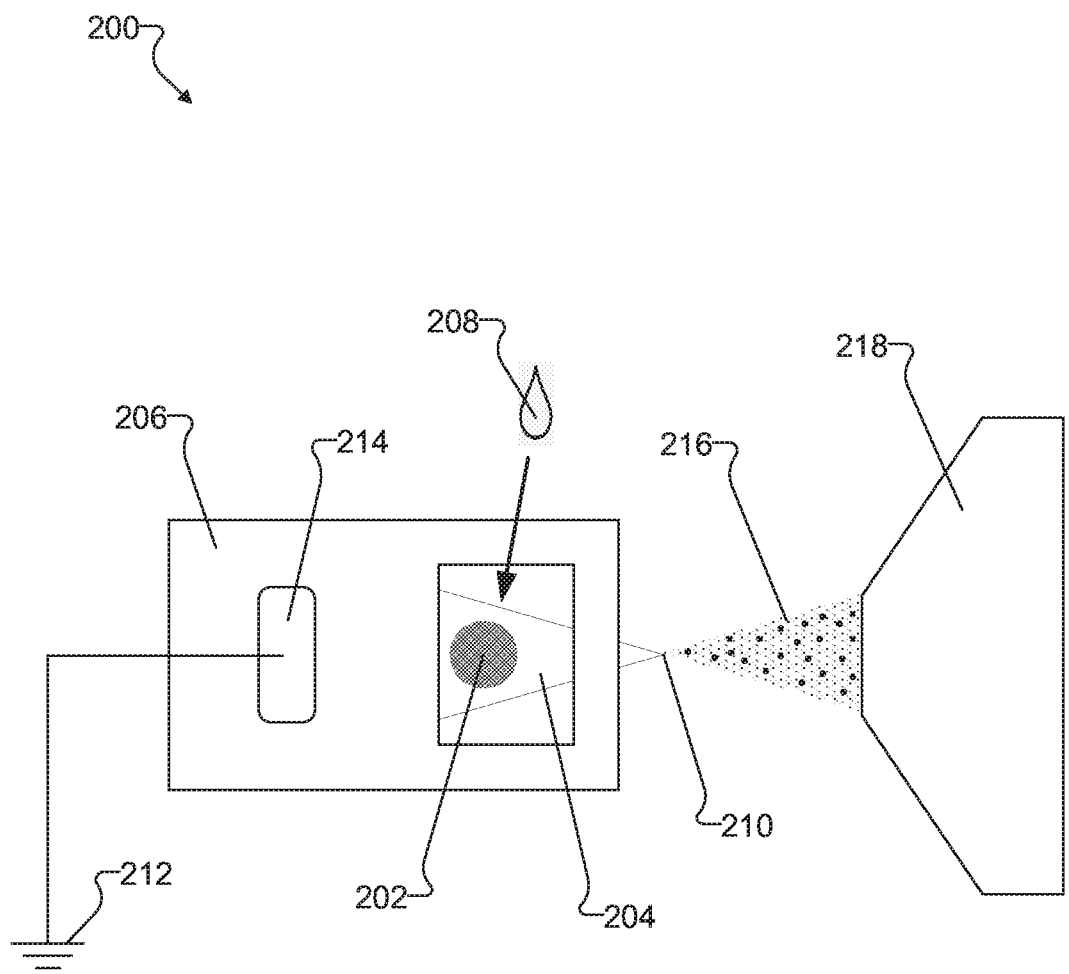
FIG. 2 illustrates an exemplary ion source that may be used within the blood sample analysis system of FIG. 1 according to principles described herein.

FIG. 2 depicts an exemplary configuration of a paper spray ion source 200. As shown, whole blood sample 202 is deposited on a surface of a porous substrate 204 (e.g., filter paper). Substrate 204 is held by cartridge 206. A solvent 208, which is configured to transport the analyte of interest to a tip 210 of substrate 204 by capillary action, may be applied to whole blood sample 202. Exemplary solvents may include, without limitation, an organic solvent (e.g., methanol), an aqueous solvent, or a mixture thereof (e.g., a methanol/water solution). Solvent 208 may be applied to the whole blood sample at any suitable time, including simultaneously with the depositing of the whole blood sample 202 on the surface of substrate 204, prior to measurement of the optical property of whole blood sample 202, or after measurement of the optical property of whole blood sample 202.

Ion source 200 may also include a voltage source 212 for applying a high voltage (e.g., about 3-5 kV) to substrate 204 via a contact hole 214 in cartridge 206. The voltage applied to substrate 204 generates ions from whole blood sample 202, including ions formed from the analyte of interest present in whole blood sample 202, and causes the ions to be emitted from tip 210 as ion beam 216 to an inlet 218 of a mass analyzer (e.g., mass analyzer 110). In some examples, the ions generated from whole blood sample 202 emitted from tip 210 in ion beam 216 may further include ions derived from one or more additional analytes of interest present in the whole blood sample.

Referring again to FIG. 1, ion source 108 may alternatively be implemented by other types of ion sources, including without limitation a matrix assisted laser desorption/ionization (MALDI) source, a solid-substrate electrospray ionization (ESI) source, and the like. Additionally or alternatively, ion source 108 may be implemented by a direct ionization source that does not apply a solvent to whole blood sample 102.

Ion source 108 may also include a cartridge mount 126 configured to hold the cartridge in a second position such that ion beam 124 emitted from substrate 104 delivers the ions to mass analyzer 110. Cartridge mount 126 may include any structures (e.g., docks, racks, trays, snaps, locks, etc.) for supporting and holding the cartridge in the second position. The cartridge may be positioned within cartridge mount 126 either manually or automatically, such as by a sample handling system, as will be described below in more detail.

Mass analyzer 110 is configured to receive the emitted ions (e.g., ion beam 124) and measure an abundance of at least one ion species corresponding to the analyte of interest present in whole blood sample 102. In some examples, mass analyzer 110 may also measure an abundance of one or more additional ion species corresponding to one or more additional analytes of interest present in whole blood sample 102. Mass analyzer 110 may be implemented by any suitable device configured to separate the received ions according to the ratio of mass to charge of each of the ions. For example, mass analyzer 110 may include, without limitation, a quadrupole ion trap mass analyzer, a quadrupole mass filter, a time-of-flight mass analyzer, an orbital electrostatic trap mass analyzer, and the like.

Mass analyzer 110 also includes an ion detector 128, which is configured to detect the separated ions and responsively generate a signal representative of ion abundance. In one example, mass analyzer 110 emits an emission beam of separated ions to ion detector 128, which is configured to detect the ions in the emission beam and generate and/or provide (e.g., to control system 112) data that may be used to construct a mass spectrum of whole blood sample 102. Additionally or alternatively, ion detector 128 may generate and/or provide (e.g., to control system 112) ion abundance data representative of the abundance of the detected ions, including the ion species corresponding to the analyte of interest present in whole blood sample 102. In some examples, ion abundance data may also be representative of the abundance of one or more additional ion species corresponding to one or more additional analytes of interest present in whole blood sample 102. Ion detector 128 may be implemented by any suitable device, including without limitation an electron multiplier, a Faraday cup, and the like.

Control system 112 is communicatively coupled with, and configured to control operations of, optical measurement unit 106, ion source 108, and/or mass analyzer 110. Control system 112 may include hardware (e.g., a processor, circuitry, memory, etc.) and/or software, integrated within a single device or distributed across multiple devices, configured to control operations of the various components of system 100 and to perform data analysis operations. For example, control system 112 may be configured to activate/deactivate light source 116 and/or light sensor 118. Control system 112 may also be configured to enable/disable ion source 108. Control system 112 may also be configured to control an oscillatory voltage power supply to supply an RF voltage to mass analyzer 110, and to control a DC power supply to supply a mass resolving DC voltage to mass analyzer 110. Control system 112 may also be configured to control mass analyzer 110 by selecting an effective range of the ratio of mass to charge of ions to detect. Control system 112 may further be configured to adjust the sensitivity of ion detector 128, such as by adjusting the gain, or to adjust the polarity of ion detector 128 based on the polarity of the ions being detected.

Control system 112 may also be configured to perform various operations associated with determining, per unit volume of blood plasma, the concentration of the analyte of interest present in whole blood sample 102. For example, control system 112 may receive, from optical measurement unit 106, optical measurement data representative of the measurement of the optical property of whole blood sample 102. Additionally or alternatively, control system 112 may receive light detection signals from optical measurement unit 106 (e.g., from light sensor 118) and generate the optical measurement data based on the received light detection signals. Control system 112 may also receive (e.g., from mass analyzer 110) and/or generate ion abundance data and use the ion abundance data in conjunction with the optical measurement data to determine the concentration of the analyte of interest per unit volume of blood plasma. For example, control system 112 may determine the hematocrit of whole blood sample 102 based on the optical measurement data, and may determine the concentration of the analyte of interest per unit volume of blood plasma based on the determined hematocrit of whole blood sample 102.

It will be understood that, due to the relationship of hematocrit with total hemoglobin, control system 112 may additionally or alternatively determine the total hemoglobin content of whole blood sample 102. The determined total hemoglobin content of whole blood sample 102 may similarly be used to determine the concentration of the analyte of interest per unit volume of blood plasma. Accordingly, references herein to hematocrit may be substituted with total hemoglobin, and these terms may be used interchangeably.

Figure 3:
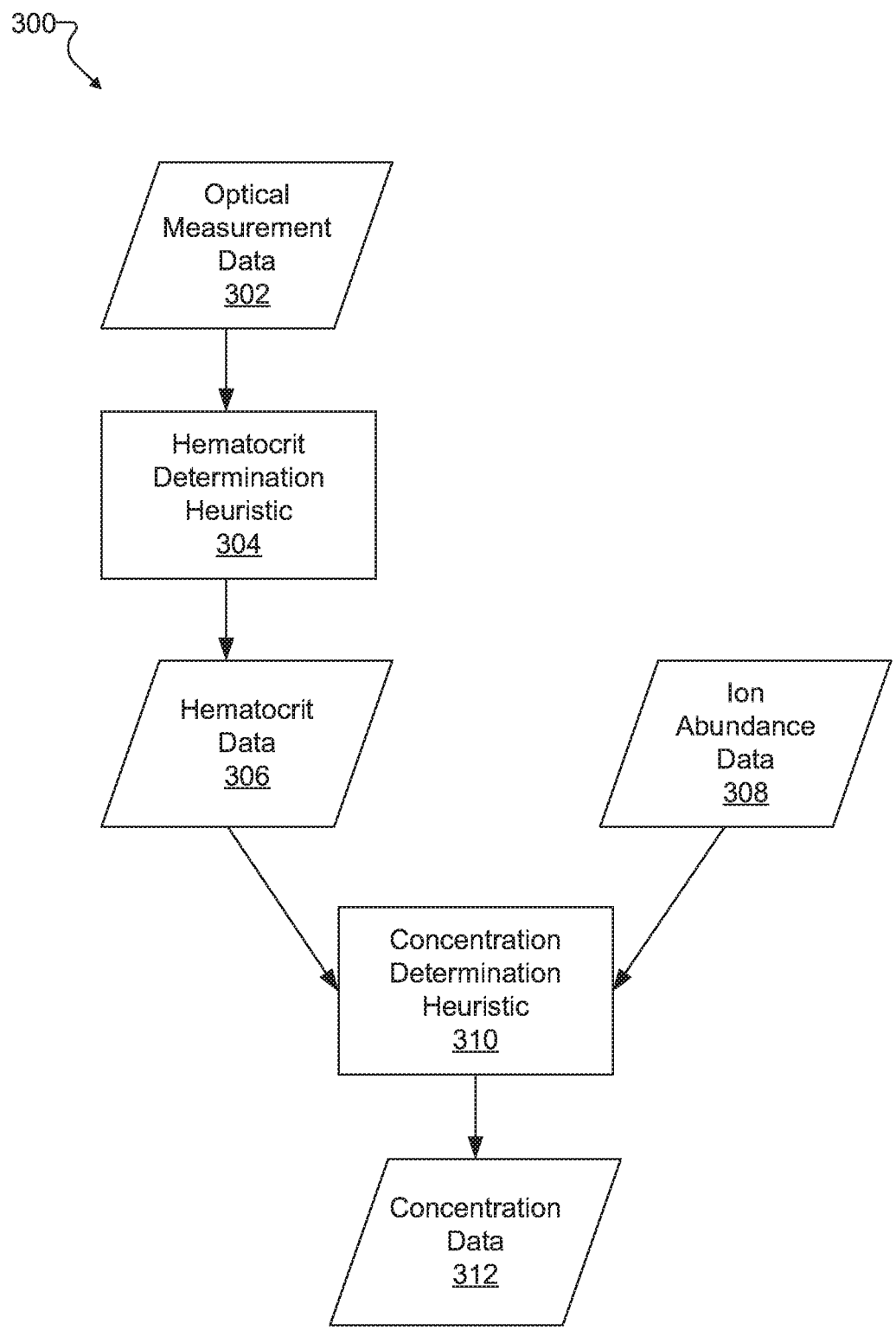
FIG. 3 illustrates an exemplary manner of determining a concentration, per unit volume of blood plasma, of an analyte of interest present in a whole blood sample according to principles described herein.

FIG. 3 shows an exemplary manner 300 in which control system 112 may determine the hematocrit of whole blood sample 102 and the concentration of the analyte of interest present in whole blood sample 102 per unit volume of blood plasma. As shown, control system 112 may apply optical measurement data 302 as an input to hematocrit determination heuristic 304. Hematocrit determination heuristic 304 may analyze the optical measurement data 302 to determine the hematocrit of whole blood sample 102 and output hematocrit data 306 representative of the determined hematocrit of whole blood sample 102.

Hematocrit determination heuristic 304 may include any suitable heuristic, process, and/or operation that may be performed or executed by control system 112 and that may be configured to determine the hematocrit of whole blood sample 102 based on optical measurement data 302. For example, hematocrit determination heuristic 304 may be based on a correlation between reflectance and/or transmittance of one or more discrete wavelengths, or a spectrum of wavelengths, by whole blood sample 102 and the hematocrit of whole blood sample 102. Because hemoglobin absorbs light, the measured reflectance and/or transmittance of whole blood sample 102 may be correlated with the amount of hemoglobin in whole blood sample 102, and the amount of hemoglobin in whole blood sample 102 may be correlated with the ratio of the volume of red blood cells to the total volume of whole blood (i.e., the hematocrit). In some examples, hematocrit determination heuristic 304 may further be based on a comparison of optical measurement data 302 with reference data (not shown) representative of reflectance and/or transmittance of a reference sample. Exemplary hematocrit determination heuristics are described in U.S. patent application Ser. No. 15/678,578, filed Aug. 16, 2017, for "System and Method for Determining Hematocrit," which is incorporated herein by reference in its entirety.

Control system 112 may also apply hematocrit data 306 and ion abundance data 308 as inputs to a concentration determination heuristic 310. Concentration determination heuristic 310 may analyze hematocrit data 306 and ion abundance data 308 to determine a concentration of the analyte of interest present in whole blood sample 102 per unit volume of blood plasma. Control system 112 may output concentration data 312 representative of the determined concentration of the analyte of interest present in whole blood sample 102 per unit volume of blood plasma.

Concentration determination heuristic 310 may include any suitable heuristic, process, and/or operation that may be performed or executed by control system 112 and that may be configured to determine, based on hematocrit data 306 and ion abundance data 308, the concentration of the analyte of interest present in whole blood sample 102 per unit volume of blood plasma. For example, concentration determination heuristic 310 may be based on a correlation between the determined hematocrit of whole blood sample 102 and the volume of whole blood sample 102 constituted by blood plasma. Whole blood generally comprises about 54% blood plasma by volume, about 45% red blood cells by volume, and less than about 1% white blood cells and platelets by volume. Therefore, the determined hematocrit of whole blood sample 102 may be used by control system 112 to convert ion abundance data 308, which represents the abundance of the ion species corresponding to the analyte of interest per unit volume of whole blood, to concentration data representative of the concentration of the analyte of interest per unit volume of blood plasma.

In one illustrative example, the relationship between the measured (whole blood) concentration, hematocrit, and plasma-equivalent concentration may be given by the following Equation [1]:

$$Z = \frac{X}{\left(1 - \frac{Y}{100}\right)} \qquad [1]$$

where X represents the measured concentration of the analyte of interest with respect to whole blood sample 102, Y represents the determined hematocrit (given as a percentage) of whole blood sample 102, and Z represents the plasma-equivalent concentration of the analyte of interest. For instance, if the concentration of creatinine in a whole blood sample is measured to be 1.3 milligrams (mg) per deciliter (dL) of whole blood and the hematocrit of the whole blood sample is determined to be 28%, the plasma-equivalent concentration of creatinine would be approximately 1.8 mg/dL of blood plasma. It will be recognized that the relationship between the measured (whole blood) concentration, hematocrit, and plasma-equivalent concentration is not limited to Equation [1], but may be represented by any suitable theoretically- or empirically-derived correlation.

In some examples, where system 100 measures the concentration of multiple analytes of interest present in whole blood sample 102, control system 112 may also determine, based on the determined hematocrit of the whole blood sample and ion abundance data 308 representative of the measured abundance of one or more additional ion species corresponding to one or more additional analytes of interest present in whole blood sample 102, a concentration of the one or more additional analytes of interest per unit volume of blood plasma.

While control system 112 is shown in FIG. 1 as a separate component of system 100, control system 112 may be implemented by or distributed across any one or more other components of system 100, such as optical measurement unit 106 and/or mass analyzer 110. Additionally or alternatively, control system 112, or any of its functions, may be implemented by a computing device external to system 100 (e.g., a remote server).

Figure 4:
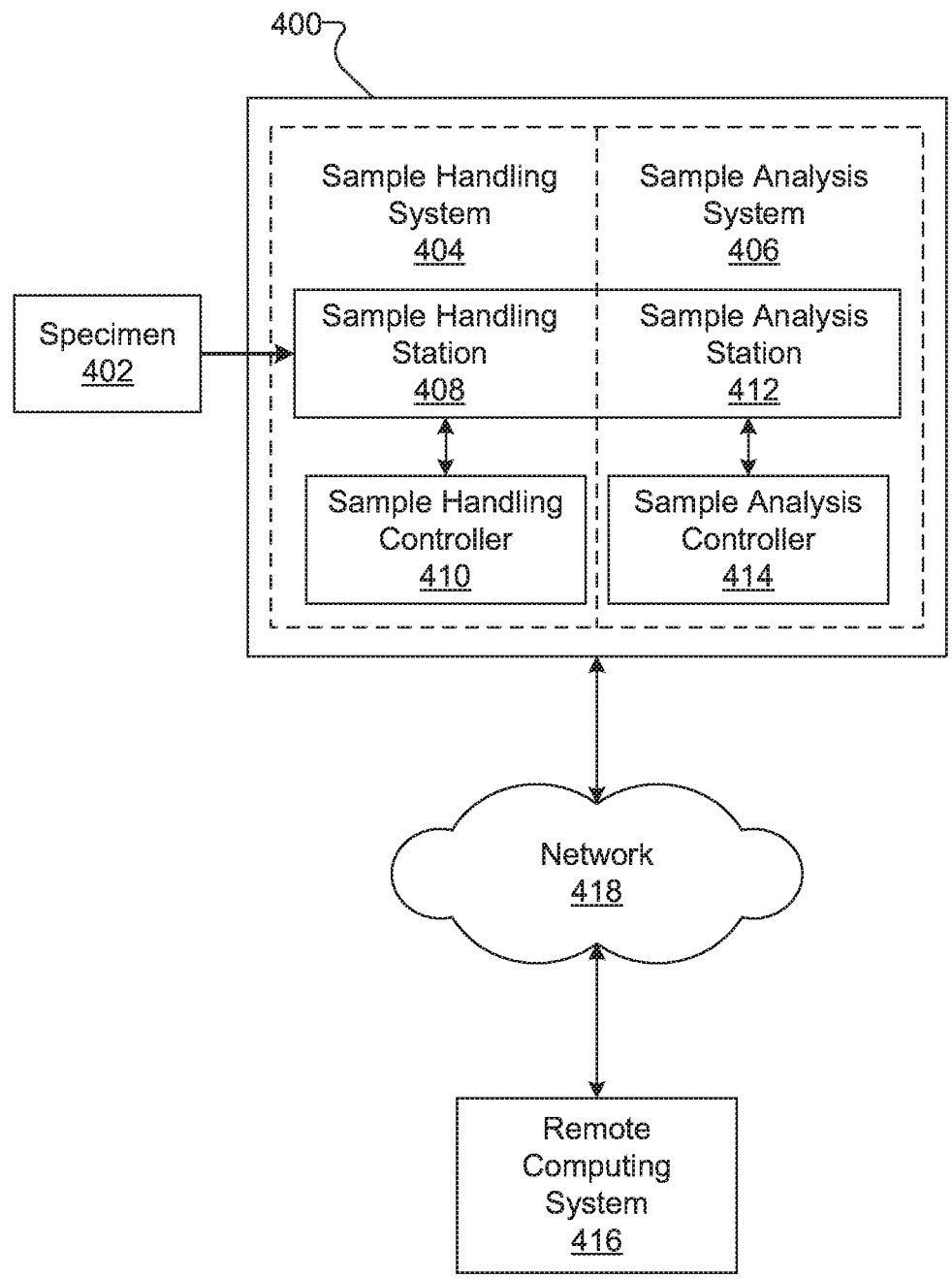
FIG. 4 illustrates an exemplary automated blood test system according to principles described herein.

Blood sample analysis system 100 may be incorporated in an automated blood test system. FIG. 4 illustrates functional components of an exemplary automated blood test system 400 ("system 400"). System 400 is configured to automatically prepare a whole blood sample from a specimen 402 of whole blood and analyze the prepared whole blood sample according to a predetermined assay selected from a variety of different or unique assays.

System 400 includes a sample handling system 404 and a sample analysis system 406. Sample handling system 404 includes a sample handling station 408 and a sample handling controller 410 that controls selected functions or operations of sample handling station 408. Sample handling station 408 is configured to prepare a whole blood sample from specimen 402 according to the selected assay and transport the whole blood sample to a sample analysis station 412 of sample analysis system 406.

Sample analysis system 406 includes sample analysis station 412 and a sample analysis controller 414 that controls selected functions or operations of sample analysis station 412. Sample analysis station 412 is configured to receive the whole blood sample from sample handling station 408 and analyze the whole blood sample according to the selected assay. In some examples, sample analysis system 406 may be implemented by system 100 described above. For example, sample analysis station 412 may include optical measurement unit 106, ion source 108, and mass analyzer 110, and sample analysis controller 414 may be implemented by control system 112.

Although sample handling system 404 and sample analysis system 406 are shown as two opposing sides of system 400, sample handling system 404 and sample analysis system 406 may be integrated such that they encompass at least some of the same area or footprint of system 400.

Additionally, although sample handling controller 410 and sample analysis controller 414 are shown as two separate controllers, in some examples sample handling controller 410 and sample analysis controller 414 may be implemented by a single controller, or by more than two controllers. Additionally or alternatively, sample handling controller 410 and/or sample analysis controller 414 may be implemented by one or more computing devices located externally to or remotely from system 400, such as a server device.

System 400 may also be communicatively connected with a remote computing system 416 by way of a network 418. Remote computing system 416 may include one or more computing devices (e.g., servers, personal computers, laptop computers, tablet computers, mobile devices, etc.) configured to receive and process assay data representative of the results of the selected assay (e.g., hematocrit data 306 and/or concentration data 312). For example, remote computing system 416 may be configured to provide, for presentation by a display screen, the assay data. Additionally or alternatively, remote computing system 416 may be configured to store assay data and provide the assay data for selective access by a user or by another computing system. In some examples, remote computing system 416 may be included in a laboratory information management system ("LIMS"), which may be configured to maintain data associated with a patient, the provisioning of health care to the patient, and/or performance of the selected assay. Alternatively, remote computing system 416 may be a computing device associated with a clinician, or it may be included in an insurance system maintained by or associated with an insurance provider.

Network 418 may be a local area network, a wireless network (e.g., Wi-Fi), a wide area network, the Internet, a cellular data network, and/or any other suitable network. Data may flow between components connected to network 418 using any communication technologies, devices, media, and protocols as may serve a particular implementation.

Although not shown in FIG. 4, system 400 may also be communicatively connected with one or more peripheral devices, including but not limited to a printer, a display device (e.g., a monitor, a projector, a television, a flat panel display, etc.), a storage device (e.g. an external hard drive, a flash drive, a disk drive, etc.), a computing device, a fax machine, a speaker, and the like. Accordingly, system 400 may be configured to output assay data to a peripheral device. For examples, system 400 may provide, for presentation by a display device, information indicating the measured concentration of the analyte of interest per unit volume of blood plasma.

System 400 may be configured to perform any suitable assay or panel of assays for specimen 402. For example, system 400 may perform a lipid panel that measures LDL-cholesterol, HDL-cholesterol, and triglycerides; a diabetes panel that measures total hemoglobin, hemoglobin A1c, and creatinine; a basic metabolic panel or a comprehensive metabolic panel; a panel of drugs of abuse and/or prescription drugs; a renal panel that measures creatinine, total hemoglobin, and at least one therapeutic drug (e.g., an immunosuppressant); a liver panel; a thyroid function panel; an electrolyte panel; and the like. In some examples, system 400 may perform a panel of assays by adjusting the range of mass to charge ratios scanned by a mass analyzer included in sample analysis system 406 to detect multiple different analytes of interest included in the whole blood sample taken from specimen 402. Additionally or alternatively, system 400 may perform a panel of assays by forming multiple different whole blood samples from specimen 402 and using various different combinations of reagents, internal standards, and/or solvents as may be required by each particular assay.

Figure 5:
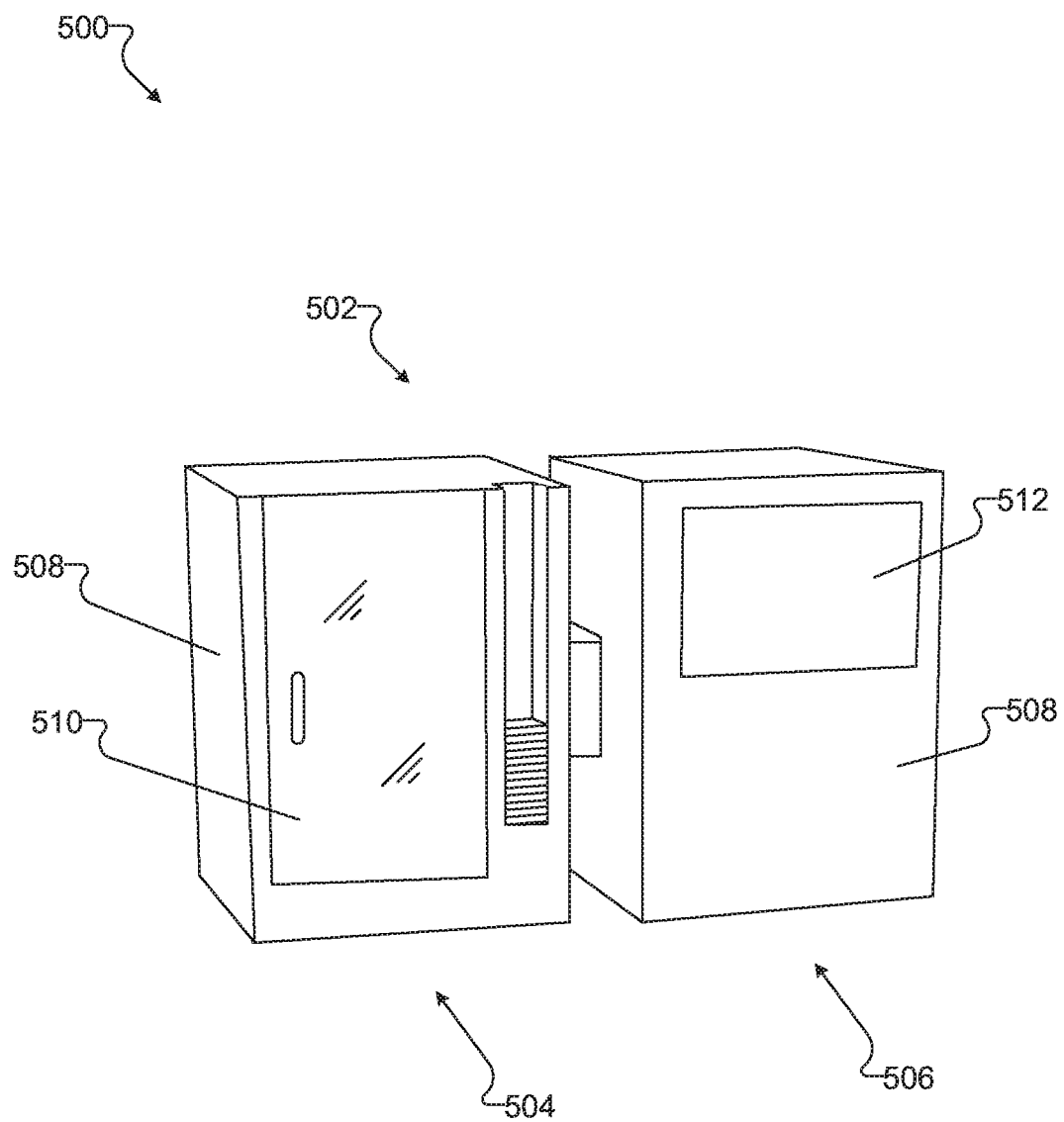
FIG. 5 illustrates a perspective view of an exemplary implementation of the automated blood test system of FIG. 4 according to principles described herein.

FIG. 5 illustrates a perspective view of an exemplary implementation 500 of system 400. As shown, an automated blood test apparatus 502 ("apparatus 502") includes a sample handling system 504 and a sample analysis system 506 housed within a cover 508. A door 510 is provided on cover 508 to allow a user to access sample handling system 504, such as to set a specimen to be analyzed or to troubleshoot operation of sample handling system 504.

A display 512 is provided on the outside of cover 508 and is configured to display information related to sample handling system 504, sample analysis system 506, and/or the selected assay. In some examples, display 512 may be a touch screen display configured to also receive user input. Additionally or alternatively, apparatus 502 may include an input device (not shown), including but not limited to a keyboard, a mouse, a control panel, a button, a touch screen, and the like.

Figure 6A:
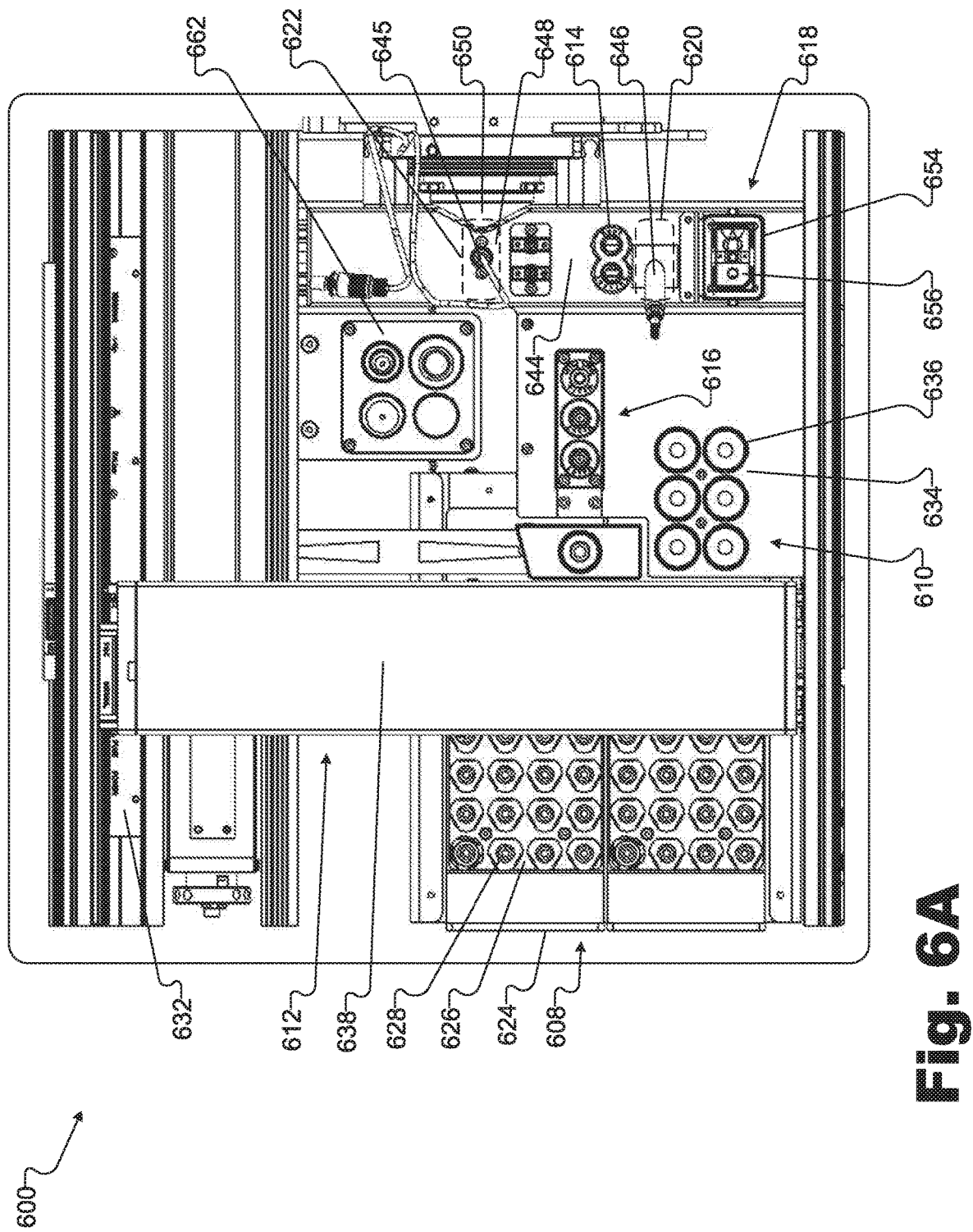
FIGS. 6A-6C illustrate views of an exemplary implementation of a sample handling system according to principles described herein.
Figure 6B:
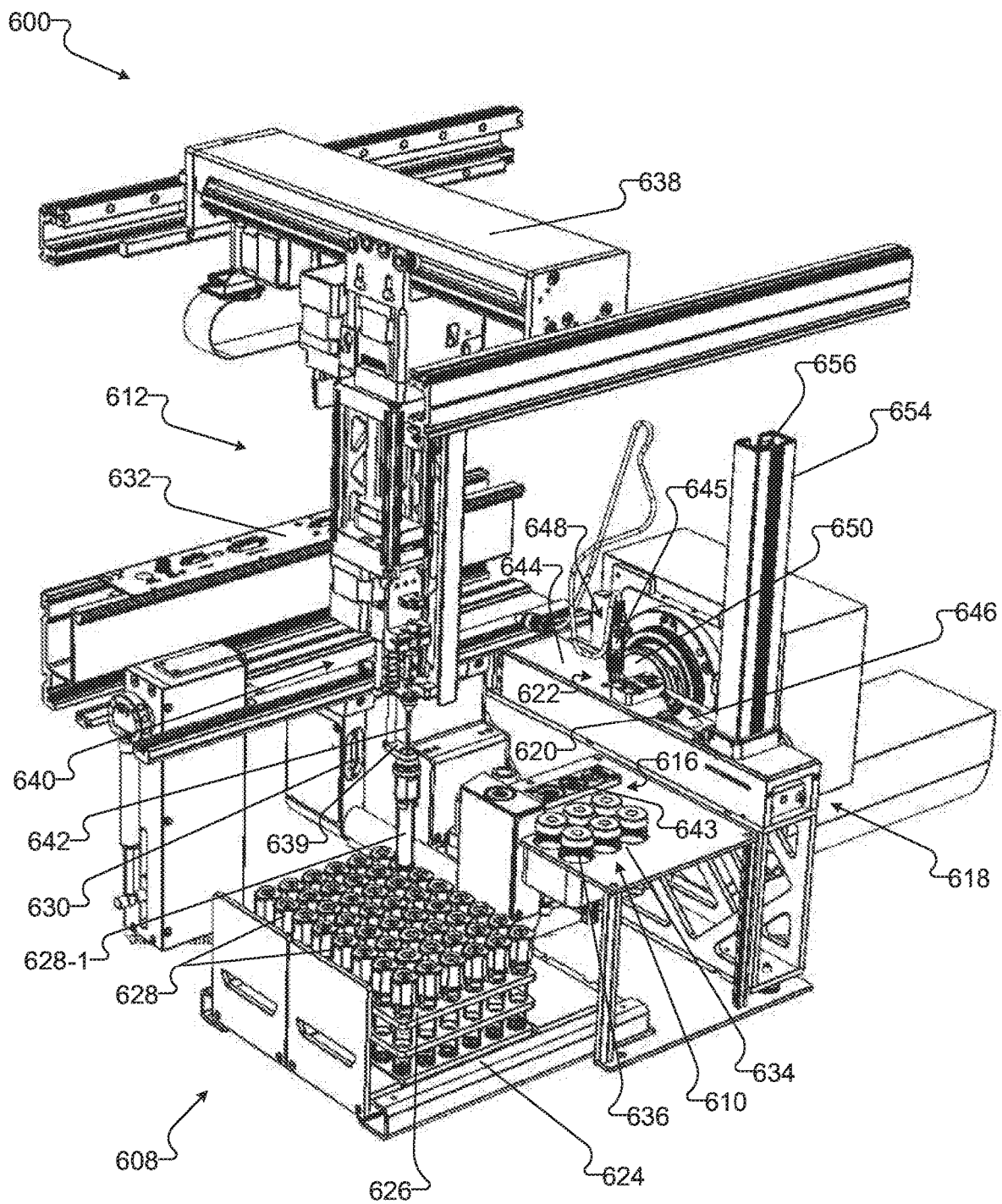
Figure 6C:
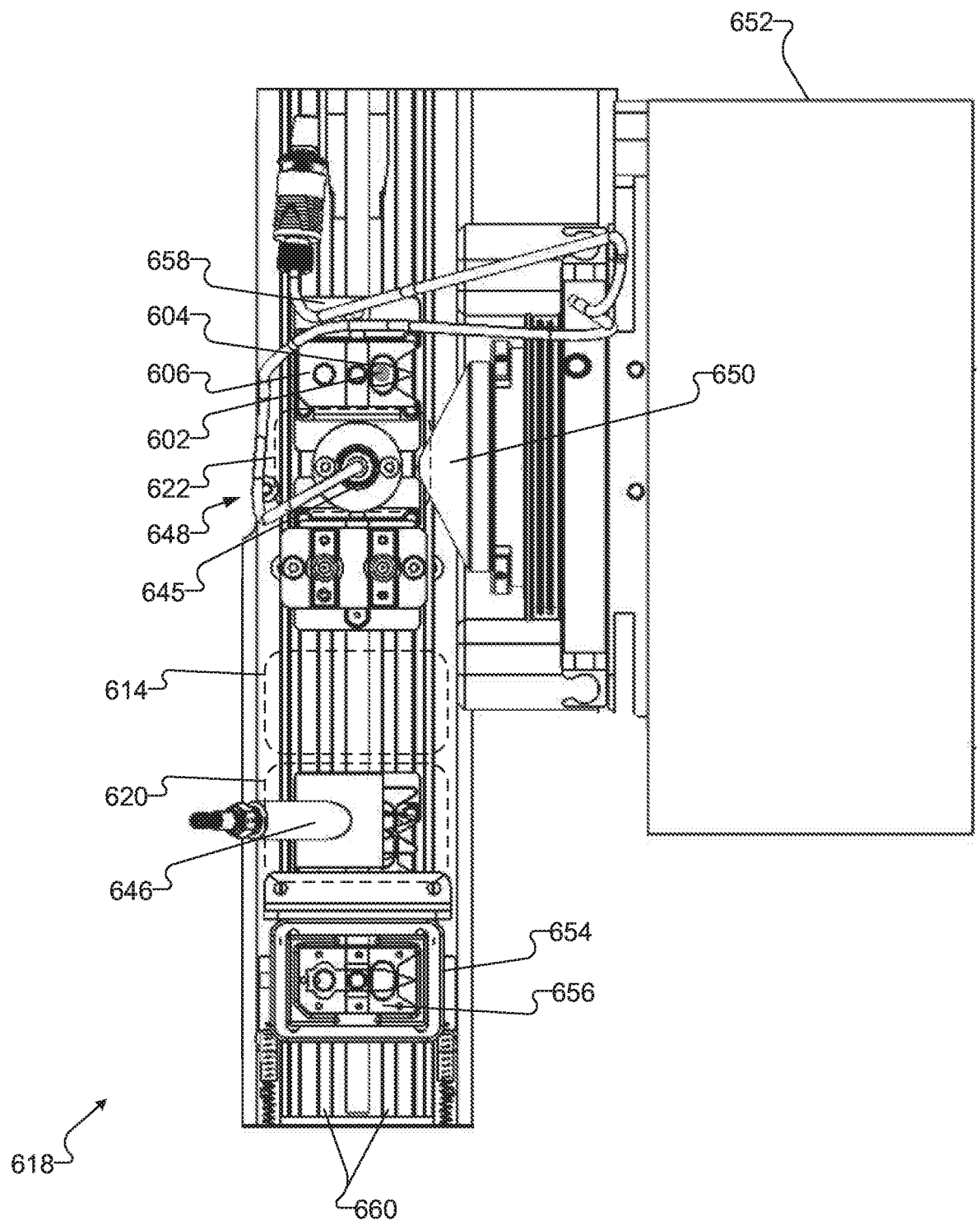

FIGS. 6A-6C illustrate an exemplary implementation of a sample handling system 600. FIG. 6A illustrates a plan view of sample handling system 600, FIG. 6B illustrates a perspective view of sample handling system 600, and FIG. 6C illustrates a closeup view of a portion of sample handling system 600 with a cover 644 removed. Sample handling system 600 is configured to deposit a whole blood sample 602 (see FIG. 6C) on the surface of a substrate 604 (see FIG. 6C) held by a cartridge 606 (see FIG. 6C) and prepare a whole blood sample 602 for analysis by a sample analysis system (e.g., a mass analyzer 652, see FIG. 6C). As shown in FIGS. 6A-6C, a sample handling station of sample handling system 600 includes a specimen station 608, a reagent station 610, an automated liquid handler 612, a sampling station 614, a wash station 616, a cartridge handler 618, an optical measurement station 620, and an ionization station 622.

Specimen station 608 includes a specimen dock 624 for holding one or more specimen trays 626, which are capable of holding one or more specimen containers 628 that each contain a specimen of whole blood collected from a patient. Specimen tray 626 may be docked in specimen dock 624 manually, or specimen tray 626 may be received from an off-line automated laboratory track system (not shown). A specimen container 628 may be any suitable labware, such as a vessel, a vial, a test tube, a cuvette, a plate, or any other suitable container.

In some examples, specimen station 608 may also include an automatic data capture system 630 (see FIG. 6B) for capturing data from a specimen container 628-1 withdrawn from specimen tray 626 by automated liquid handler 612. For example, automatic data capture system 630 may be implemented by a scanner configured to scan a label (not shown) provided on specimen container 628-1. The label may include information about the blood sample, such as but not limited to information about the patient from whom the sample was collected (e.g., name, birthdate, gender, the patient's doctor, etc.), the date the sample was collected, the type of blood test ordered for the sample, the clinician that ordered the blood test, an output destination of the blood test results (e.g., hematocrit data 306 and/or concentration data 312), and the like. In some examples, the label may include any suitable information associated with a laboratory information system. In some examples, the information on the label may be coded with a one-dimensional code (e.g., a bar code) or a two-dimensional code (e.g., a QR code) configured to be read by the scanner. Additionally or alternatively, automatic data capture system 630 may utilize radio-frequency identification (RFID) to capture data from specimen container 628-1. Automatic data capture system 630 may transmit data captured by automatic data capture system 630 to a sample handling controller 632 (see FIGS. 6A and 6B) for further processing of the captured data.

Reagent station 610 includes a reagent dock 634 for holding one or more reagent containers 636 that each contain a reagent to be used in the preparation and analysis of whole blood sample 602. For example, one or more reagents may be applied to whole blood sample 602 according to the selected assay. In some examples, reagent dock 634 may be configured to hold a reagent tray (not shown) that is capable of holding one or more reagent containers 636. Suitable reagents may include, but are not limited to, precipitation reagents (e.g., acetonitrile, methanol, perchloric acid, zinc sulfate, etc.), protein digestion reagents (e.g., serine proteases such as trypsin, threonine, cysteine, lysine, arginine, or aspartate proteases, metalloproteases, chymotrypsin, glutamic acid proteases, lys-c, glu-c, and chemotrypsin), protein stabilization agents (such as buffers, chaotropic agents, or denaturants), internal standards (e.g., stable isotope labeled analytes, heavy isotope labeled peptides, non-native peptides or analytes, structurally similar analogs, chemically similar analogs), solvents (e.g., methanol, aqueous solvents, etc.), calibration standards, controls, and cleansing solutions. According to various embodiments, one or more reagents may be pre-mixed to form a combined reagent mixture specific for a particular assay or panel of assays.

In some examples, reagent station 610 may include a cooling system (not shown) to maintain the temperature of reagent station 610 at a constant, cooled temperature (e.g., between about 4° C. and about 10° C.) to reduce the loss of volatile reagents through evaporation and thereby extend the lifetime and activity of the reagents contained in reagent containers 636.

At sampling station 614, automated liquid handler 612 is configured to deposit whole blood sample 602 on the surface of substrate 604 held by cartridge 606 and, as appropriate for the selected assay, apply one or more reagents to whole blood sample 602.

Automated liquid handler 612 may include a robot assembly 638 configured to provide at least two axes of motion. As shown, robot assembly 638 is a gantry robot, but robot assembly 638 may be any other suitable robot mechanism, including but not limited to an autosampler, a SCARA robot, a delta robot, an articulated robot, a cylindrical robot, a polar robot, and the like. Automated liquid handler 612 may further include a gripper 639 (see FIG. 6B), or other like device, to capture and release a container (e.g., a specimen container 628, a reagent container 636, etc.). Automated liquid handler 612 may also include a dispenser assembly 640 for aspirating a volume of a liquid (e.g., whole blood, a reagent, a solvent, an internal standard, a cleansing solution, etc.) from a container (e.g., specimen container 628-1, a reagent container 636, etc.) and dispensing the aspirated liquid into another container or onto whole blood sample 602 or substrate 604. Dispenser assembly 640 includes a tip 642 (e.g., a needle, a pipette, a syringe, etc.) that is movable by robot assembly 638 between two or more of specimen station 608, reagent station 610, sampling station 614, and wash station 616.

In some examples, automated liquid handler 612 may be configured to wash tip 642 at wash station 616 after each use. For example, after a sample is dispensed from tip 642, tip 642 may be washed by one or more aspirations of a cleansing solution stored in a wash container 643 at wash station 616 and dispensing of the cleansing solution at wash station 616. Alternatively, tip 642 may be a disposable tip that may be ejected by dispenser assembly 640 after dispensing a liquid. Dispenser assembly 640 may then acquire a new disposable tip from a tip storage station (not shown).

As shown in FIGS. 6A and 6B, a cover 644 is provided to shield optical measurement unit 646 from ambient light, and also covers ion source 648. Accordingly, cover 644 also covers portions of cartridge handler 618. FIG. 6C shows a closeup plan view of cartridge handler 618 with cover 644 removed. Referring to FIG. 6C, cartridge handler 618 is configured to position cartridge 606 at sampling station 614 where automated liquid handler 612 may deposit whole blood sample 602 on the surface of substrate 604. Cartridge handler 618 is further configured to position cartridge 606 at optical measurement station 620 where optical measurement unit 646 may measure the optical property of whole blood sample 602. Cartridge handler 618 is further configured to position cartridge 606 at ionization station 622 where ion source 648 may generate ions from whole blood sample 602 and cause the ions to be emitted from substrate 604 toward an inlet 650 of mass analyzer 652.

To this end, cartridge handler 618 may include a cartridge magazine 654 that holds a plurality of blank cartridges 656 (i.e., cartridges holding blank substrates on which no blood sample has been deposited). In some examples, cartridge magazine 654 may be loaded with blank cartridges 656 manually. Cartridge magazine 654 dispenses the next available blank cartridge 656 onto a moveable carriage 658. A blank cartridge 656 mounted in carriage 658 is referred to herein as cartridge 606. Carriage 658 of cartridge handler 618 is configured to hold cartridge 606 and is moveable along a fixed rail (or track) 660 between cartridge magazine 654, sampling station 614, optical measurement station 620, and ionization station 622. Accordingly, carriage 658 is configured to position cartridge 606 at sampling station 614, optical measurement station 620, and ionization station 622. In some examples, carriage 658 may correspond to cartridge mount 122 and/or cartridge mount 126 of system 100 (see FIG. 1).

Movement of carriage 658 along rail 660 may be driven by a motor assembly (not shown). Any suitable combination of motors, gears, belts, transmissions, and the like may be used to drive movement of carriage 658. Alternatively, cartridge handler 618 may be configured to move and position cartridge 606 by any other means as may suit a particular implementation, such as a robot assembly (e.g., a linear robot, a gantry robot, a SCARA robot, a delta robot, an articulated robot, a cylindrical robot, a polar robot, etc.).

An illustrative operation of sample handling system 600 will now be described. The description that follows is merely exemplary and is not limiting. A user may provide user input to commence a blood sample analysis of one or more whole blood specimens contained specimen containers 628. Upon receipt of the user input, cartridge handler 618 may dispense a blank cartridge 656 from cartridge magazine 654 into carriage 658, and then move carriage 658 to position the mounted cartridge 606 at sampling station 614. Additionally, automated liquid handler 612 may withdraw specimen container 628-1 from specimen tray 626 and pass specimen container 628-1 by automatic data capture system 630 (e.g., a scanner) to capture information associated with specimen container 628-1. In some examples automated liquid handler 612 may rotate or otherwise adjust the position of specimen container 628-1 until the information on specimen container 628-1 has been captured. If the information on specimen container 628-1 cannot be acquired, automated liquid handler 612 may replace specimen container 628-1 in specimen tray 626, and sample handling controller 632 may indicate the position in the tray of the unanalyzed specimen container 628-1 and/or notify an operator (e.g., via a display unit) of the error.

If the information on specimen container 628-1 is successfully captured by automatic data capture system 630, sample handling controller 632 may determine, based on the captured information, the selected assay for the specimen and may continue processing of the specimen in accordance with the selected assay. For example, automated liquid handler 612 may cause tip 642 to pierce the cap of specimen container 628-1 and aspirate an aliquot (e.g., about 5-10 µL) of the whole blood specimen from specimen container 628-1 and dispense, at sampling station 614, the aspirated whole blood onto substrate 604 to form whole blood sample 602. Automated liquid handler 612 may then wash tip 642 at wash station 616. In some examples, after tip 642 has aspirated an aliquot of the whole blood specimen from specimen container 628-1, automated liquid handler 612 may also aspirate, at reagent station 610, a volume of an internal standard into tip 642 prior to dispensing whole blood sample 602. Thus, the whole blood sample and internal standard may mix in tip 642 and/or when dispensed together to form whole blood sample 602.

In some embodiments, it may be necessary to mix the whole blood specimen contained in specimen container 628 prior to aspirating and depositing the whole blood sample on the surface of substrate 604. For example, blood specimens may partition over time, such as by separation of blood cells (red blood cells, white blood cells, etc.) from the plasma, and some analytes of interest (e.g., therapeutic drugs, drugs of abuse, etc.) may be distributed unequally between the blood cells and the plasma. To this end, automated liquid handler 612 may cause the whole blood specimen contained in specimen container 628-1 to be mixed. Any suitable mixing method may be used. In some examples, automated liquid handler 612 may position specimen container 628 at a mixing station 662 (see FIG. 6A), which may mix the whole blood specimen prior to sampling. Mixing station 662 may include any suitable mixer, such as a vortex mixer or a shaker. Additionally or alternatively, automated liquid handler 612 may mix the whole blood specimen by aspirating and dispensing the whole blood specimen contained in specimen container 628 a number of times with tip 642 of dispenser assembly 640. The number of aspirations may depend on the volume of the specimen container 628, the aspiration volume, and the dispensing "speed." In other embodiments, automated liquid handler 612 may shake specimen container 628.

After automated liquid handler 612 has deposited whole blood sample 602 on the surface of substrate 604 held by cartridge 606, cartridge handler 618 may move carriage 658 to position cartridge 606 at optical measurement station 620 for measurement, by optical measurement unit 646, of an optical property of whole blood sample 602. Optical measurement unit 646 may then transmit data and/or signals of the measurement result to a sample analysis controller (e.g., sample analysis controller 414), which may determine the hematocrit of whole blood sample 602 based on the measured optical property of whole blood sample 602.

In some examples cartridge handler 618 may move carriage 658 to position cartridge 606 at sampling station 614 again for application of one or more reagents to whole blood sample 602. In some examples, sample handling controller 632 may specify, based on the selected assay, the particular reagent(s) (e.g., precipitation reagents, internal standards, and solvents) for automated liquid handler 612 to apply to whole blood sample 602.

For example, sample handling controller 632 may direct automated liquid handler 612 to apply a precipitation reagent to whole blood sample 602 to aid in the precipitation of blood components other than the analyte of interest and trap such blood components onto the surface of substrate 604. For example, the precipitation reagent may be a solution of zinc sulfate ($ZnSO_4$) in methanol, which may trap heavy proteins present in whole blood sample 602 onto the surface of substrate 604. Exemplary precipitation reagents and methods of applying the precipitation reagents are described in U.S. patent application Ser. No. 15/609,606, filed May 31, 2017 for "Method of Analyzing a Wet Blood Sample," which is incorporated herein by reference in its entirety. By applying a precipitation reagent to whole blood sample 602, a wet whole blood sample 602 may be analyzed. Furthermore, the precipitation reagent may prevent interference from unwanted blood components during measurement of the concentration of the analyte of interest. Accordingly, automated liquid handler 612 may aspirate a precipitation reagent at reagent station 610 and dispense the precipitation reagent onto whole blood sample 602 at sampling station 614.

Alternatively, after whole blood sample 602 has been deposited on the surface of substrate 604, sample handling system 600 may allow whole blood sample 602 to dry on the surface of substrate 604 before application of any reagents or ionization of whole blood sample 602 by ion source 648. When whole blood sample 602 is dried on substrate 604, components (e.g., proteins) of whole blood sample 602 other than the analytes of interest may adhere to substrate 604 and thus not enter mass analyzer 652 when whole blood sample 602 is ionized. Therefore, in some examples sample handling system 600 may include a dryer (not shown) for drying whole blood sample 602 on the surface of substrate 604. The dryer may be implemented by any suitable device, including without limitation a fan and/or a heater. The dryer may be configured to dry whole blood sample 602 on the surface of substrate 604 either before measurement of the optical property by optical measurement unit 646 or after optical measurement but before ionization by ion source 648. Alternatively, whole blood sample 602 may be allowed to air dry over time without the use of a dryer. However, drying whole blood sample 602 takes time and thus prolongs the turn-around time for the blood test.

While the optical measurement of the optical property of whole blood sample 602 has been described as occurring prior to application of the precipitation reagent or prior to drying of whole blood sample 602, the optical measurement may alternatively occur after application of the precipitation reagent or after drying of whole blood sample 602.

After application of a precipitation reagent and/or drying of whole blood sample 602, automated liquid handler 612 may also apply an ionization solvent to whole blood sample 602. For example, automated liquid handler 612 may aspirate an ionization solvent at reagent station 610 and dispense the ionization solvent onto whole blood sample 602 at sampling station 614. Automated liquid handler 612 may then wash tip 642 at wash station 616 for use in processing the next whole blood specimen.

Cartridge handler 618 may then move carriage 658 to position cartridge 606 at ionization station 622 where ion source 648 may apply a high voltage (e.g., about 4.5 kV) to substrate 604. Ion source 648 may include a high voltage pin 645 configured to contact substrate 604 via a contact hole in cartridge 606 and apply a high voltage (e.g., about 3-5 kV) to the ionization solvent applied to whole blood sample 602. The applied voltage generates ions from whole blood sample 602, including ions formed from an analyte of interest present in whole blood sample 602, and causes the ions to be emitted from substrate 604 toward inlet 650 of mass analyzer 652. Mass analyzer 652 may then measure, based on a ratio of mass to charge (m/z) of the ions emitted from substrate 604, an abundance of at least one ion species corresponding to the analyte of interest. The measured abundance may be in the form of an ion current, or the height or area of a peak in the mass spectrum at the m/z of the analyte of interest. As noted above, an internal standard, for example an isotopically-labeled version of the analyte molecule, may be added to the whole blood sample in a known amount, and the measured abundance may be determined in accordance with the ratios of the heights or areas of peaks located at the m/z's of the analyte of interest and its corresponding internal standard, or via use of stored calibration curves. A sample analysis controller (e.g., sample analysis controller 414) may then determine, based on the determined hematocrit of the whole blood sample and the measured abundance of the at least one ion species, a concentration of the analyte of interest per unit volume of blood plasma.

Cartridge handler 618 may then dispose of cartridge 606 at a waste station (not shown) and move carriage 658 back to cartridge magazine 654 for processing of the next whole blood specimen. Sample handling system 600 may then select and process the next specimen container 628 in specimen tray 626 in like manner.

The foregoing description of sample handling system 600 is merely illustrative and is not limiting. Indeed, various modifications may be made to sample handling system as may suit a particular implementation. For example, any one or more of the operations of sample handling system 600 may be performed manually. For example, an operator may manually position cartridge 606 at sampling station 614, at optical measurement station 620, and/or at ionization station 622 by inserting cartridge 606 into a corresponding cartridge mount. Additionally or alternatively, a user may manually provide input to activate and/or control movement of any of the components of sample handling system 600.

Additionally, sample handling system 600 may include any number of automated liquid handlers, robot assemblies, dispenser assemblies, and tips as may suit a particular implementation. For example, each different liquid used in system 400 (e.g., a whole blood sample, a precipitation reagent, a solvent, and the like) may be aspirated and dispensed by a separate dispenser assembly.

Figure 7:
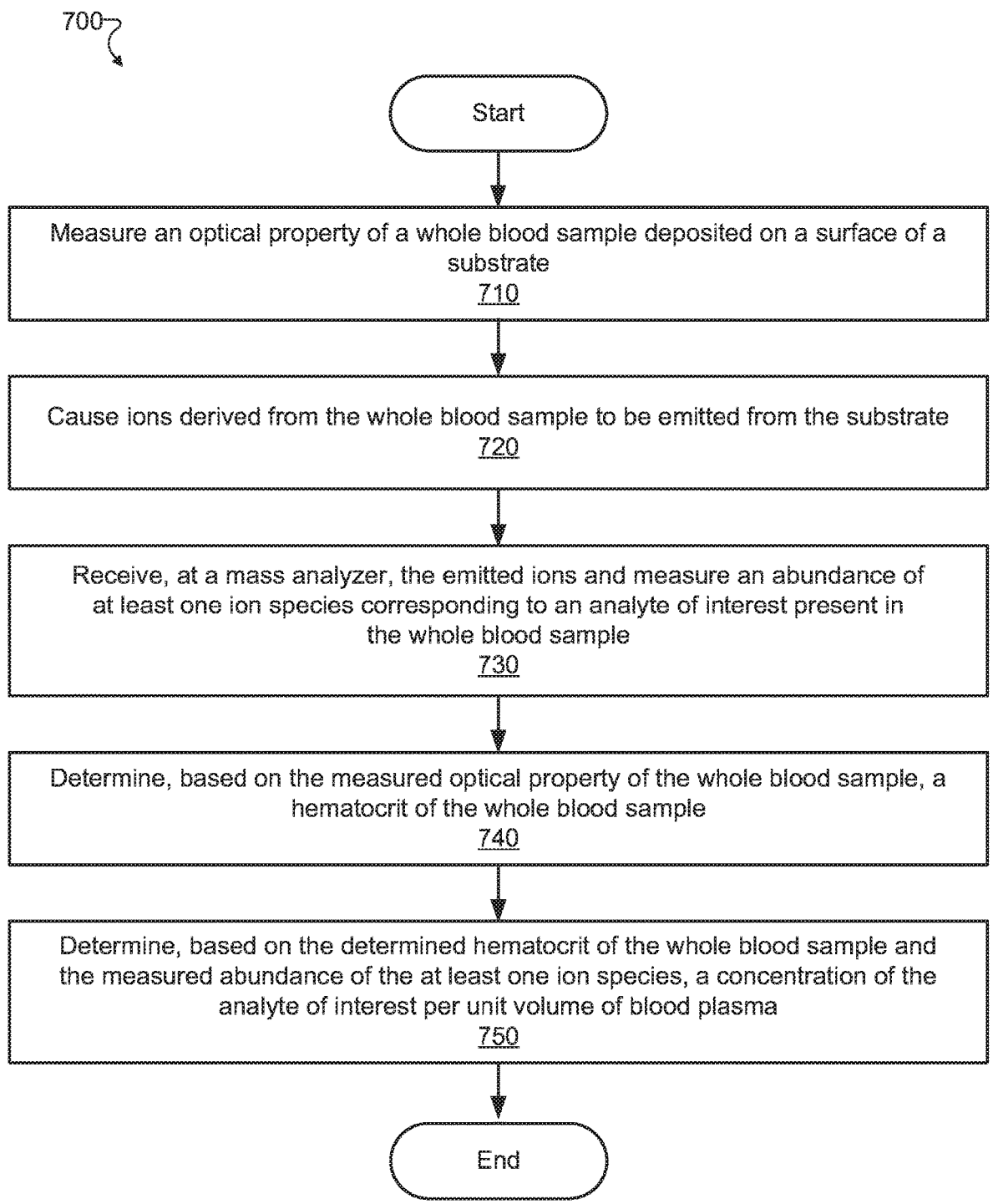
FIG. 7 illustrates an exemplary method of determining a concentration, per unit volume of blood plasma, of an analyte of interest present in a whole blood sample according to principles described herein.

FIG. 7 shows an exemplary method of performing a blood test to measure, per unit volume of blood plasma, a concentration of an analyte of interest present in a whole blood sample. While FIG. 7 identifies exemplary steps according to one embodiment, other embodiments may omit, add to, reorder, combine, and/or modify any of the steps shown in FIG. 7.

In step 710, an optical property of a whole blood sample deposited on a surface of a substrate is measured. This may be performed in any manner described herein.

In step 720, ions derived from the whole blood sample are caused to be emitted from the substrate. This may be performed in any manner described herein. The ions emitted from the substrate include ions formed from an analyte of interest present in the whole blood sample.

In step 730, the ions emitted from the substrate are received at a mass analyzer and an abundance of at least one ion species corresponding to the analyte of interest is measured by the mass analyzer. This may be performed in any manner described herein.

In step 740, a hematocrit of the whole blood sample is determined based on the measured optical property. This may be performed in any manner described herein.

In step 750, a concentration of the analyte of interest per unit volume of blood plasma is determined based on the determined hematocrit of the whole blood sample and the measured abundance of the at least one ion species. This may be performed in any manner described herein.

In certain embodiments, one or more of the systems, components, and/or processes described herein may be implemented and/or performed by one or more appropriately configured computing devices. To this end, one or more of the systems and/or components described above may include or be implemented by any computer hardware and/or computer-implemented instructions (e.g., software) embodied on at least one non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), electrically erasable programmable read-only memory ("EPROM"), FLASH-EEPROM, any other memory chip or cartridge, or any other tangible medium from which a computer can read.

Figure 8:
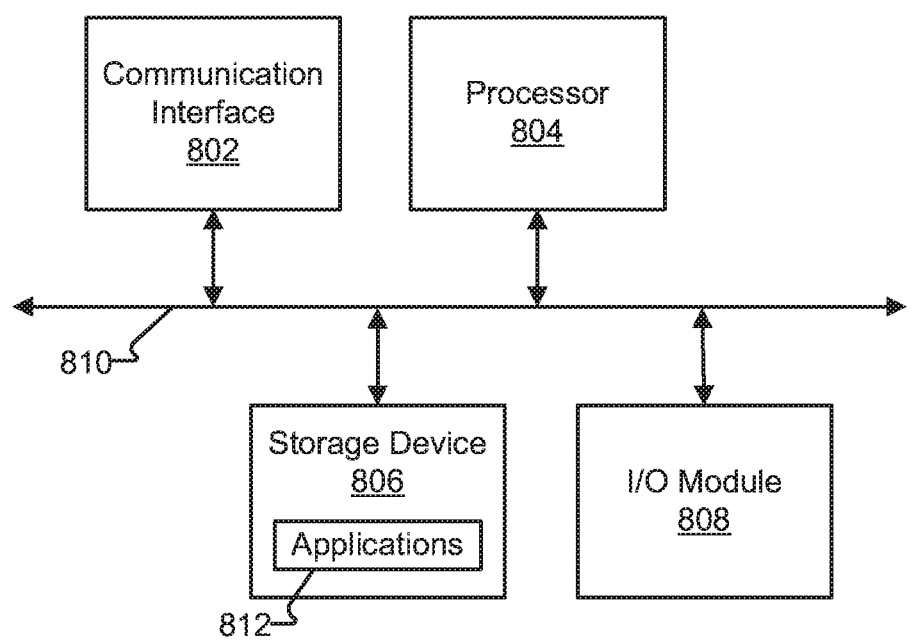
FIG. 8 illustrates an exemplary computing system according to principles described herein.

FIG. 8 illustrates an exemplary computing device 800 that may be specifically configured to perform one or more of the processes described herein. As shown in FIG. 8, computing device 800 may include a communication interface 802, a processor 804, a storage device 806, and an input/output ("I/O") module 808 communicatively connected via a communication infrastructure 810. While an exemplary computing device 800 is shown in FIG. 8, the components illustrated in FIG. 8 are not intended to be limiting. Additional or alternative components may be used in other embodiments. Components of computing device 800 shown in FIG. 8 will now be described in additional detail.

Communication interface 802 may be configured to communicate with one or more computing devices. Examples of communication interface 802 include, without limitation, a wired network interface (such as a network interface card), a wireless network interface (such as a wireless network interface card), a modem, an audio/video connection, and any other suitable interface.

Processor 804 generally represents any type or form of processing unit capable of processing data or interpreting, executing, and/or directing execution of one or more of the instructions, processes, and/or operations described herein. Processor 804 may direct execution of operations in accordance with one or more applications 812 or other computer-executable instructions such as may be stored in storage device 806 or another computer-readable medium.

Storage device 806 may include one or more data storage media, devices, or configurations and may employ any type, form, and combination of data storage media and/or device. For example, storage device 806 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 806. For example, data representative of one or more executable applications 812 configured to direct processor 804 to perform any of the operations described herein may be stored within storage device 806. In some examples, data may be arranged in one or more databases residing within storage device 806.

I/O module 808 may include one or more I/O modules configured to receive user input and provide user output. One or more I/O modules may be used to receive input for a single virtual reality experience. I/O module 808 may include any hardware, firmware, software, or combination thereof supportive of input and output capabilities. For example, I/O module 808 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 808 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 808 is configured to provide graphical data to a display for presentation to a user. The graphical data may be representative of one or more graphical user interfaces and/or any other graphical content as may serve a particular implementation.

In some examples, control system 112 (see FIG. 1), sample handling controller 410 (see FIG. 4), sample analysis controller 414 (see FIG. 4), and sample handling controller 632 (see FIGS. 6A and 6B) may be implemented by or within one or more components of computing device 800. For example, one or more applications 812 residing within storage device 806 may be configured to direct processor 804 to perform one or more processes or functions associated with control system 112, sample handling controller 410, sample analysis controller 414, and/or sample handling controller 632. Likewise, a storage device or memory of control system 112, sample handling controller 410, sample analysis controller 414, and/or sample handling controller 632 may be implemented by storage device 806 or a component thereof.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow.

For example, the exemplary systems and methods described above are not limited to determining the hematocrit of the whole blood sample deposited on the surface of the substrate based on the measured optical property (e.g., reflectance and/or transmittance) of the whole blood sample. Rather, the systems and methods described above may measure the hematocrit of the whole blood sample electrically (e.g., by measuring conductivity of the whole blood sample), electrochemically, and/or by ultrasound.

Additionally, the exemplary systems and methods described herein are not limited to analysis of a blood sample, but may also be used with other types of samples, such as a urine sample. For example, in accordance with the systems and methods described herein, a urine sample may be deposited on the surface of a substrate and analyzed by a mass spectrometer (e.g., mass spectrometer 114) to determine a concentration of one or more analytes of interest (e.g., creatinine, a performance enhancing drug, etc.) included in the urine sample. While some aspects of whole blood sample analysis may not be applicable or useful for a urine analysis (e.g., optical measurement of an optical property of the urine sample, application of a precipitation reagent, etc.), the systems and methods described herein may be used with multiple different types of samples. For example, the systems and methods described herein may analyze both a whole blood sample and a urine sample from the same patient, thus providing comprehensive information to a clinician with a short turnaround time.

Additionally, certain features of one embodiment described herein may be combined with or substituted for features of another embodiment described herein. The description and drawings are accordingly to be regarded in an illustrative rather than a restrictive sense.

What is claimed is:

1. A system comprising:
   an optical measurement unit configured to measure an optical property of a liquid whole blood sample deposited on a surface of a substrate;
   an ion source configured to cause ions directly from the liquid whole blood sample to be emitted from the substrate, wherein the ions emitted from the substrate include ions formed from an analyte of interest present in the liquid whole blood sample;
   a mass analyzer configured to receive the ions emitted from the substrate and measure an abundance of at least one ion species corresponding to the analyte of interest; and
   at least one computing device configured to
      determine, based on the measured optical property, a hematocrit of the liquid whole blood sample, and
      determine, based on the determined hematocrit of the liquid whole blood sample and the measured abundance of the at least one ion species, a concentration of the analyte of interest per unit volume of blood plasma.

2. The system of claim 1, wherein the optical measurement unit comprises:
   a light source configured to emit light to the liquid whole blood sample, and
   a light sensor configured to detect at least one of (i) light reflected by the liquid whole blood sample and (ii) light transmitted through the liquid whole blood sample.

3. The system of claim 2, wherein the light source comprises a light emitting diode (LED), a laser, an incandescent lamp, a discharge lamp, or a combination thereof.

4. The system of claim 1, wherein the optical measurement unit comprises an optical spectrometer.

5. The system of claim 1, wherein the ion source includes a voltage source for applying a voltage to the substrate.

6. The system of claim 5, further comprising an automated liquid handler for applying a solvent to the liquid whole blood sample.

7. The system of claim 6, wherein the substrate comprises a layer of porous material such that components of the liquid whole blood sample are transported along the substrate by capillary action after the solvent is added to the liquid whole blood sample.

8. The system of claim 6, wherein the automated liquid handler further applies one or more of a reagent and an internal standard to the liquid whole blood sample.

9. The system of claim 1, wherein
   the substrate is held by a cartridge,
   the optical measurement unit is further configured to support, during the measurement of the optical property of the liquid whole blood sample, the cartridge in a first position such that light emitted by the optical unit is incident on the liquid whole blood sample, and
   the ion source is further configured to support, during the emission of the ions from the substrate, the cartridge in a second position such that the ions are delivered to the mass analyzer.

10. The system of claim 9, further comprising a carriage configured to move the substrate from the first position to the second position.

11. The system of claim 1, wherein the analyte of interest present in the liquid whole blood sample comprises hemoglobin A1c or creatinine.

12. The system of claim 1, wherein
   the ions emitted from the substrate further include ions derived from one or more additional analytes of interest present in the liquid whole blood sample,
   the mass analyzer is further configured to measure an abundance of one or more additional ion species corresponding to the one or more additional analytes of interest, and
   the at least one computing device is further configured to determine, based on the determined hematocrit of the liquid whole blood sample and the measured abundance of the one or more additional ion species, a concentration of the one or more additional analytes of interest per unit volume of blood plasma.

13. The system of claim 12, wherein the analyte of interest and the one or more additional analytes of interest comprise components of a renal panel comprising creatinine, total hemoglobin, and an immunosuppressant.

14. The system of claim 12, wherein the analyte of interest and the one or more additional analytes of interest comprise components of a diabetes panel comprising hemoglobin A1c, creatinine, and total hemoglobin.

15. The system of claim 12, wherein the analyte of interest and the one or more additional analytes of interest are included in a panel of drugs of abuse.

16. The system of claim 1, wherein the mass analyzer comprises a quadrupole ion trap mass analyzer, a quadrupole mass filter, a time-of-flight mass analyzer, or an orbital electrostatic trap mass analyzer.

17. The system of claim 1, wherein the at least one computing device is further configured to provide, for presentation to a user, information indicating the concentration of the analyte of interest per unit volume of blood plasma.

18. The system of claim 1, further comprising:
an automated liquid handler configured to
   withdraw a volume of liquid whole blood from a liquid whole blood specimen contained in a specimen container, and
   deposit the liquid whole blood sample on the surface of the substrate.

19. A method, comprising:
measuring, by a blood sample analysis system, an optical property of a liquid whole blood sample deposited on a surface of a substrate;
determining, by the blood sample analysis system based on the measured optical property, a hematocrit of the liquid whole blood sample;
causing, by the blood sample analysis system, ions directly from the liquid whole blood sample to be emitted from the substrate, the ions emitted from the substrate including ions of an analyte of interest present in the liquid whole blood sample;
receiving, by the blood sample analysis system at a mass analyzer, the ions emitted from the substrate;
measuring, by the blood sample analysis system at the mass analyzer, an abundance of at least one ion species corresponding to the analyte of interest; and
determining, by the blood sample analysis system based on the determined hematocrit of the liquid whole blood sample and the measured abundance of the at least one ion species, a concentration of the analyte of interest per unit volume of blood plasma.

\* \* \* \* \*